(12) United States Patent
Anderson et al.

(10) Patent No.: US 7,387,893 B2
(45) Date of Patent: *Jun. 17, 2008

(54) VECTORS, CELLS AND PROCESSES FOR PYRIMIDINE DEOXYRIBONUCLEOSIDES PRODUCTION

(75) Inventors: David Martin Anderson, Rockville, MD (US); Lin Liu, Rockville, MD (US); Sergey Podkovyrov, Gaithersburg, MD (US); Baomin Wang, Rockville, MD (US)

(73) Assignee: SmithKline Beecham Corporation, Philadelphia, PA (US)

( * ) Notice: Subject to any disclaimer, the term of this patent is extended or adjusted under 35 U.S.C. 154(b) by 267 days.

This patent is subject to a terminal disclaimer.

(21) Appl. No.: 10/914,529

(22) Filed: Aug. 9, 2004

(65) Prior Publication Data
US 2005/0009083 A1    Jan. 13, 2005

Related U.S. Application Data

(62) Division of application No. 10/018,878, filed as application No. PCT/GB00/02357 on Jun. 30, 2000, now Pat. No. 6,777,209.

(51) Int. Cl.
| | |
|---|---|
| C12N 15/00 | (2006.01) |
| C12N 1/20 | (2006.01) |
| C12N 5/10 | (2006.01) |
| C07H 21/00 | (2006.01) |
| C12N 9/02 | (2006.01) |
| C12N 9/12 | (2006.01) |
| C12N 9/78 | (2006.01) |
| C12Q 1/26 | (2006.01) |
| C12P 21/06 | (2006.01) |
| C07K 14/00 | (2006.01) |

(52) U.S. Cl. .............. 435/320.1; 435/252.3; 435/325; 435/252.33; 435/189; 435/25; 435/69.1; 435/194; 435/227; 536/23.2; 530/350

(58) Field of Classification Search .......... 435/189, 435/25, 320.1, 69.1, 325, 252.3, 194, 227, 435/252.33; 536/23.2; 530/350
See application file for complete search history.

(56) References Cited

FOREIGN PATENT DOCUMENTS

| | | |
|---|---|---|
| EP | 0329062 | 8/1989 |
| EP | 0344937 | 12/1989 |
| WO | WO 91/09130 | 6/1991 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Allen et al, "T-4 RIBO Nucleotide Reductase Physical and Kinetic Linkage to Other Enzymes of Deoxy RIBO Nucleotide Biosynthesis", *Journal of Biological Chemistry* 255:16 7583-7588 (1980).
Carreras et al., "The catalytic mechanism and structure of thymidylate synthase", *Annual Review of Biochemistry*, US, Palto Alto, CA 64:721-762 (1995).
Follman, "Enzymatic reduction of ribonucleotides: biosynthesis pathway of deoxyribonucleotides", *Angewandte Chemie, International Edition, De, Verlag Chemie, Weinheim* 13:9 569-579 (Sep. 1974).
Heidhardt et al., "*Escherichia coli* and *Salmonella*" ASM Press, *American Society for Microbiology*, Washington, DC Chapter 35; J. Neuhard and R.A. Klein, Biosynthesis and conversion of pyrimidines, pp. 580-599 (1996).
Holmgren, "Glutathione Dependent Enzyme Reactions of the Phage T-4 RIBO Nucleotide Reductase System" *Journal of Biological Chemistry* 253:20 7424-7430 (1978).
Ji et al., "T4 Phage Ribonucleotide Reductase Allosteric Regulation In-vivo by Thymidine Triphosphate", *Journal of Biological Chemistry* 266:25 16289-16292 (1991).
Tseng et al., "Total Sequence Flanking Regions and Transcripts of Bacteriophage T4 NRDA Gene Coding for Alpha Chain of Ribonucleoside Diphosphate Reductase", *Journal of Biological Chemistry* 263:31 16242-16251 (1988).
Bork, "Powers and pitfalls in sequence analysis: the 70% hurdle," *Genome Research* 10:398-400 (2000).
Broun et al., "Catalytic plasticity of fatty acid modification enzymes underlying chemical diversity of plant lipids," *Science* 282:1315-1317 (1998).
Lim et al., "Improvement of heterologous protein productivity by controlling postinduction specific growth rate in recombinant *Escherichia coli* under control of the $P_L$ promoter," Biotechnol. Prog. 14:548-553 (1998).

(Continued)

*Primary Examiner*—Delia M. Ramirez
(74) *Attorney, Agent, or Firm*—Michael M. Conger

(57) ABSTRACT

Novel DNA constructs and host cells comprising the same are disclosed. DNA constructs comprise a transcription unit (e.g. operon) comprising DNA sequences encoding for ribonucleotide reductase and thioredoxin or a uridine kinase gene and/or a dCTP deaminase gene. In preferred embodiments the constructs comprising DNA sequences encoding for ribonucleotide reductase and thioredoxin further comprise DNA sequences encoding for thymidylate synthase and/or transcription units comprising sequences encoding for uridine kinase preferably together with dCTP deaminase. In particularly preferred embodiments, the host cells comprise constructs having all of the above characteristics wherein the host cell displays repressed or no uracil DNA glycosylase activity. This may be achieved by removal of the host cell ung gene. Use of host cells in the manufacture of pyrimidine deoxyribonucleotides e.g. thymidine is also disclosed.

4 Claims, 6 Drawing Sheets

OTHER PUBLICATIONS

Seffernick et al., "Melamine deaminase and atrazine chlorohydrolase: 98 percent identical but functionally different," *J. Bacteriol.* 183:2405-2410 (2001).

Van de Loo et al., "An oleate 12-hydroxylase from *Ricinus communis* L. is a fatty acyl desaturase homolog," *Proc. Natl. Acad. Sci.* 92:6743-6747 (1995).

Wang et al., "*dcd* (dCTP Deaminase) gene of *Escherichia coli*: mapping, cloning, sequencing, and identification as a locus of suppressors of Lethal *dut* (dUTPase) mutations," *J. Bacteriol.* 174(17):5647-5653 (1992).

* cited by examiner

VECTORS, CELLS AND PROCESSES FOR PYRIMIDINE DEOXYRIBONUCLEOSIDES PRODUCTION

This application is a divisional of U.S. application Ser. No. 10/018,878 filed Mar. 6, 2002, now U.S. Pat. No. 6,777,209, which was filed pursuant to 35 U.S.C. § 371 as a United States National Phase Application of International Application No. PCT/GB00/02357 filed Jun. 30, 2000, which claims priority from U.S. Ser. No. 09/345,492 filed Jul. 1, 1999, and U.S. Ser. No. 60/141,827 filed Jul. 1, 1999.

FIELD OF THE INVENTION

The present invention relates to the production of pyrimidines, purines and derivatives thereof e.g. deoxyribonucleosides, using genetically modified cells comprising novel DNA constructs.

BACKGROUND OF THE INVENTION

Thymidine is useful as a pharmaceutical intermediate, particularly for the chemical synthesis of azidothymidine ("AZT," sold under the trademark ZIDOVUDINE). Although ZIDOVUDINE-type AZT was one of the first therapies developed for HIV/AIDS, it continues to have important and expanded use (Langreth, R., *The Wall Street Journal*, Nov. 21, 1995, pp B12). ZIDOVUDINE-type AZT is valuable particularly when used in combination therapies such as a combination with lamivudine (also known as 3TC), sold under the trademark EPIVIR. This lamvudine and 3TC combination is sold under the trademark COMBIVIR. Although the HIV virus can mutate to form resistance to either AZT or 3TC, COMBIVIR-type nucleotide-analog combination is particularly effective because the reverse transcriptase apparently cannot be resistant to both nucleoside analogues at the same time (Larder, B. A. et al., *Science* 269: 696-699, 1995). ZIDOVUDINE-type AZT is also useful in conjunction with HIV protease inhibitor type drugs (Waldholz, M., *The Wall Street Journal*, Jan. 30, 1996, pp B1), and in the treatment of HIV infected pregnant women in order to reduce the frequency of infection of the fetus at birth. In 1997 about 600,000 children died of AIDS contracted from their mothers at birth. ZIDOVUDINE-type AZT taken for several months prior to birth can reduce the transmission of the virus to infants by two-thirds. Thymidine produced by chemical synthesis used in the manufacture of AZT is a very significant cost.

In U.S. Pat. No. 5,213,972 (McCandliss & Anderson, hereinafter "the '972 patent"), the entire contents of which are incorporated herein by reference and to which the reader is specifically referred, a process for the production of pyrimidine deoxyribonucleoside (PdN) is disclosed (see in particular examples 7 to 14 of the '972 patent). A replicatable microorganism comprising and expressing a DNA sequence encoding a pyrimidine deoxyribonucleotide phosphohydrolase that converts a PdN monophosphate to a pyrimidine deoxyribonucleoside is taught. More particularly, McCandliss & Anderson, supra, describe a fermentation method that can be used to produce thymidine that involves the expression of deoxythymidylate phosphohydrolase (dTMPase) from the Bacillus bacteriophage PBS1. This type of enzyme has been found in nature expressed by bacteriophages that do not contain thymidine in their DNA, but instead incorporates compounds like deoxyuridine or hydroxymethyldeoxyuridine.

In the thymidine fermentation described in the '972 patent, the enzymes that degrade thymidine (thymidine phosphorylase and uridine phosphorylase) have been removed by mutation so that thymidine accumulates. Thus, the use of the dTMPase enzyme helps create the pathway to allow thymidine synthesis. An expression of dTMPase alone, however, may not assure a commercially viable level of thymidine production. Accordingly, there is a continuing need to enhance the production of thymidine by cells expressing dTMPase in order to make thymidine production by fermentation commercially viable, by lowering the production cost relative to the current chemical synthesis methods.

The biochemical pathway for pyrimidine deoxynucleotide production, for example, in *E. coli* is highly regulated at the levels of transcription and translation as well as at the protein level by mechanisms including attenuation, feedback inhibition and enzyme activation. Neuhard, J. and R. A. Kelln, Biosynthesis and Conversion of Pyrimidines, Chapter 35 [In] Neidhardt, F. C. et al. [eds] "*Escherichia coli* and *Salmonella* Cellular and Molecular Biology", Second Edition, Vol. I, pp580-599, ASM Press, Washington D.C., 1996. The expression of dTMPase and elimination of thymidine breakdown by mutations in the deoA (thymidine phosphorylase), udp (uridine phosphorylase) and tdk (thymidine kinase) genes and therefore resulting expression products results in thymidine synthesis in *E. coli* but not at a commerically viable level.

SUMMARY OF THE INVENTION

The biosynthesis of purines and pyrimidines involves a common step of reducing a ribonucleoside diphosphate (in some species triphosphate) to its corresponding deoxy analog. In the overall process the reduction of the ribose moiety to 2-deoxyribose requires a pair of hydrogen atoms which are ultimately donated by NADPH and H$^+$. However, the immediate electron donor is not NADPH but the reduced form of a heat stable protein called thioredoxin or glutaredoxin and at least one other unidentified source since the *E. coli* ribonucleotide reductase system still works in trxA (thioredoxin) grx (glutaredoxin) double mutants (Neuhard and Kelln, supra). The reducing equivalents of the reduced thioredoxin are transferred to ribonucleoside diphosphate reductase which carries out the reduction process. Manipulation of, for example, this step could prove useful in improving the commerical production of purine and pyrimidine deoxynucleosides.

It is an object of the present invention to provide novel DNA constructs e.g.vectors and genetically modified microorganisms comprising said vectors particularly for use in the production of recoverable amounts, especially commercially useful amounts, of pyrimidine and purine deoxynucleosides.

It is also an object of the present invention to provide processes which represent an improvement over McCandliss and Anderson described supra.

In accordance with one aspect of the present invention there is provided a DNA construct comprising a transcriptional unit which comprises a ribonucleotide reductase gene and a thioredoxin gene or a uridine kinase gene and/or a dCTP deaminase gene.

In one embodiment the DNA construct comprises a transcriptional unit which comprises a ribonucleotide reductase gene and a thioredoxin gene.

In another embodiment the DNA construct comprises a transcriptional unit which comprises a uridine kinase gene and/or a dCTP deaminase gene.

Preferably the DNA construct comprises a transcriptional unit which comprises a uridine kinase gene and a dCTP deaminase gene.

Most preferably the DNA construct comprises a transcriptional unit which comprises a ribonucleotide reductase gene and a thioredoxin gene and a uridine kinase gene and a dCTP deaminase gene.

In accordance with another aspect of the present invention there is provided a modified host cell comprising a DNA construct according to the invention.

In accordance with yet another aspect of the present invention there is provided a culture medium comprising the modified host cells of the invention and processes for the production of a purine or pyrimidine, for example thymidine, comprising the use of said modified host cells.

In one embodiment the host cells comprise a DNA construct which construct comprises a transcription DNA unit (e.g. operon) which unit comprises DNA sequences encoding for ribonucleotide reductase and thioredoxin in which said reductase preferably displays less sensitivity to allosteric inhibition than a wild type host cell equivalent or counterpart wherein said cell further comprises one or more of the following features:

(a) a transcription unit (e.g. operon), preferably located on said DNA construct, comprising DNA sequences encoding for (and preferably heterologous with respect to host cell equivalent) thymidylate synthase;

(b) a transcription unit (e.g. operon), preferably located on said DNA construct, comprising DNA sequences encoding for uridine kinase and preferably dCTP deaminase; and (c) repressed or absent Uracil DNA glycosylase activity.

In another embodiment the DNA construct for use in the production of recoverable amounts of pyrimidine and derivatives thereof, in particular pyrimidine deoxyribonucleosides such as thymidine, comprises a transcription unit (e.g. operon) which unit comprises (preferably heterologous) DNA sequences encoding for uridine kinase and/or dCTP deaminase.

Genetically modified host cells comprising and expressing the construct and culture medium comprising the modified host cells are also provided.

This aspect is based, in part, on the observation that host cells comprising DNA encoding for uridine kinase and/or dCTP deaminase, optionally togaher with additional genes as suggested in U.S. Pat. No. 5,213,972 required for thymidine production, lead to a significant improvement in thymidine production.

The respective aspects of the present invention disclose for the first time a plurality of advances on the teaching of U.S. Pat. No. 5,213,972 to provide improved DNA constructs and host cells comprising the constructs for use in the commercial production of pyrimidine deoxyribonucleosides, particularly thymidine.

Other objects, features and advantages of the present invention will become apparent from the following description. It should be understood, however, that these represent preferred embodiments of the invention and are by way of illustration only. Various modifications and changes within the spirit and scope of the invention will become apparent to those skilled in the art.

PREFERRED EMBODIMENTS OF THE INVENTION

The construct of the present invention may be chromosomal or more preferably extra-chromosomal e.g. located on a vector.

Vectors of the present invention include plasmid, virus, transposons, minichromosome or phage, preferably plasmid. The vector comprising the transcription unit may be introduced into the host cell according to any convenient method known to those skilled in the art, e.g. P1 transduction, electroporation or transformation. Suitable host cells useful in the present invention include eukaryotes and prokaryotes (e.g. Bacterium). Prokaryotes include *E. coli, Salmonella, Pseudomonas, Bacillus*, strains and mutants thereof. *E.coli* is preferred due to the large amount of information, genetic tools and mutant alleles that are available. It is particularly preferred that a method of transduction is available for the host cell of choice to enable mutations to be readily moved from one host cell to another and facilitate genetic mutation of the host without requiring direct mutation whenever a new mutation is desired.

The present inventors have found that the use of bacteriophage T4 nrdA, nrdB and nrdC genes are particularly useful for encoding the reductase and thioredoxin in *E. coli*. See Sjöberg, B. M. et al., *EMBO J.*, 5:2031-2036 (1986); Tseng, M.-J., et a., *J. Biol. Chem.* 263:16242-16251 (1988); and LeMaster, D. M., *J. Virol.* 59:759-760 (1986). More specifically, a very significant improvement in *E. coli* thymidine production was achieved through the cloning and expression of the T4 bacteriophage nrdA and nrdB genes coding for ribonucleotide reductase together with T4 nrdC coding for thioredoxin since the T4 ribonucleotide reductase cannot use *E. coli* thioredoxin. The T4-coded ribonucleotide reductase was found to be relatively insensitive to control by allosteric inhibition in vitro compared to the *E. coli* enzyme (Berglund, O., *J. Biol. Chem.* 247:7276-7281,1972). For example, unlike the *E. coli* enzyme (Berglund, O., *J. Biol. Chem.* 247: 270-7275, 1972) the T4 ribonucleotide reductase is not inhibited by dATP, but actually stimulated by dATP and ATP (Berglund, O., *J. Biol. Chem.* 247:7276-7281, 1972).

DNA sequences encoding for the ribonucleotide reductase (e.g. nrdA and nrdB genes) and thioredoxin (e.g. nrdC gene) are preferably heterologous with respect to host cell DNA and preferably derived from T phage (preferably *E. coli* T bacteriophage), particularly T "even" phages e.g. T2, T4 or T6. See Campbell, A. M., Bacteriophages, Chapter 123, In Neidherdt, supra; and Mathews, C. K. et al. (eds.) Bacteriaophage T4, American Society of Microbiology, Washington, D.C., 1983. The term "derived from" is intended to define not only a source in the sense of its physical origin but also to define material which has structural and/or functional characteristics which correspond to material originating from the reference source.

Another useful feature of the T even phage enzyme is its substrate specificity. The normal *E. coli* ribonucleotide reductase uses UDP as a substrate only poorly since the $K_m$ for UDP is about 10 fold higher for UDP than CDP (Neuhard and Kelln, supra). However, the T4 enzyme has only a two-fold difference in $K_m$ (Berglund, O., *J. Biol. Chem.* 247: 7276-7281, 1972) between CDP and UDP substrates allowing two routes to dUTP synthesis. Although there have been attempts to obtain functional expression of T4 ribonucleotide reductase in *E. coli*, previous efforts were only successful in expressing the components separately and could demonstrate activity only by mixing in vitro (Tseng, M.-J., P. He, J. M. Hilfinger, and G. R. Greenberg, *J. Bacteriol*. 172: 6323-6332, 1990). Whilst not being bound by theory, the inventors believe that perhaps due to the lack of the usual pattern of feedback inhibition, expression of T4 ribonucleotide reductase in *E. coli* is lethal and it must be carefully conditionally expressed. Further envisaged are genes that encode precursor forms of the reductase and/or thioredoxin which are processed to produce a mature form. Such processing may proceed via various intermediate forms.

Vectors of the present invention preferably comprise a regulatory element (e.g. promoter such as lambda $P_L$, operator, activator, repressor such as lambda repressor, particularly a temperature sensitive variant, and/or enhancer), appropriate termination sequences initiation sequences and ribosome binding sites. The vector may further comprise a selectable marker. Alternatively, regulatory elements (particularly lambda repressor) may be located on the host cell chromosome. It is preferred that nrdA and nrdB are arranged in the vector downstream (in terms of reading frame) from nrdC. In particular, it is preferred that nrdB is arranged downstream from nrdA. Thus a most preferred arrangement is a vector comprising an operon comprising nrdCAB.

The T4 ribonucleotide reductase is not devoid of feedback-control in viva (J. Ji, R. G. Sargent, and C. K. Mathews, *J.Biol.Chem.* 266:16289-16292,1991; and Berglund supra). To promote ribonucleoside diphosphate reduction further e.g. for thymidine production, the gene coding for the regulatory subunit, nrdA, may be modified by, for example, a mutational approach to create an enzyme capable of increased thymidine production due to e.g. a reduced sensitivity to allosteric inhibition for example inhibition by the enzyme's immediate product or inhibition by a product resulting from a downstream event.

In order to construct T4 nrdA mutants, site-directed mutagenesis may be used to modify or change (e.g. substitute) gene bases encoding amino acids suspected to alter e.g. dTTP binding site involved in allosteric regulation. Analysis of the amino acid sequence of T4 ribonucleotide reductase revealed a segment that appears to fit well with a postulated consensus sequence thought to be involved in dTTP binding (E. M. McIntosh and R. H. Haynes, *Mol. Cell. Biol.* 6:1711-1721, 1986). Several changes may be made in this region of the T4 ribonucleotide reductase using oligonucleotide-directed mutagenesis. The general approach may be modelled after the effort of More et al. (More, J. T., J. M. Ciesla, L.-M. Changchien, G. F. Maley and F. Maley, *Biochemistry* 33: 2104-2112, 1994) to reduce the dTTP binding of deoxycytidylate deaminase. One mutation, [79]Ala to Ile, in the T4 nrdA appeared to be very useful. For example, the thymidine productivity of strains containing the [79]Ala to Ile mutant in T4 nrdA evaluated by a shake flask fermentation method was significantly increased. As demonstrated below, the present inventors achieved at least 25% increase over the parent strain without this single change.

Although the [79]Ala to Ile is one successful example, those skilled in the art will now realize that many other amino acid changes to this region are now possible to obtain the desired effect, that being to putatively disrupt dTTP binding, but not disrupt the enzyme's basic functionality. For example, substitution of [79]Ala with other amino acids displaying similar side chains to Ile (e.g. leucine, valine) may be utilized. Modifications of position 79 in conjunction with other modifications (e.g. mutations) within the postulated consensus region are also envisaged. Deletion of one or more amino acid positions in the consensus region and introduction of synthetic DNA into the region are other approaches available to those skilled in the art.

In another aspect of the present invention there is provided a host cell comprising a construct which construct (e.g. vector) comprises a transcriptional unit comprising DNA sequences encoding for heterologous ribonucleotide reductase and thioredoxin which reductase is less sensitive to allosteric inhibition than the wild type host cell equivalent or counterpart. It will be apparent to those skilled in the art that determining the relative sensitivity of a candidate heterologous reductase to allosteric inhibition compared to the wild type host cell equivalent is a matter of routine experimentation and observation.

Transcription units comprising the DNA sequences e.g. nrdA, nrdB and nrdC genes are preferably operons wherein the nrd genes are arranged in tandem. This permits transcription of these genes as a single mRNA transcript. In order to minimize unproductive energy expenditure by the host cell and further to minimize plasmid size, it is preferred that the operon contains only genetic sequences required in the encoding of reductase and thioredoxin (including any regulatory or control elements). This may necessitate the removal of superfluous DNA (for example, the unusual intron in the phage T4 nrdB gene, Sjoberg, B-M., et al EMBO J.5: 2031-2036,1986).

In other preferred embodiments, vectors of the present invention for use in for example the production of thymidine further comprise DNA sequences encoding for thymidylate synthase (e.g. the td gene). See e.g. Chu, F. K. et al., *Proc. Natl. Acad. Sci. USA* 81:3049-3053 (1984); Chu, F. K. et al., *J. Bacteriol.* 169:4368-4375 (1987). The purpose of using this enzyme is to improve control over the levels of deoxyuridine produced and in particular the relative impurity level of deoxyuridine relative to thymidine. The dTMPase enzyme is not completely specific for dTMP. With a higher $K_m$ than for dTMP, the PBS1 dTMPase will also utilize dUMP as substrate to produce deoxyuridine (Price, A. R., *Methods in Enzymol.* 51: 285-290,1978). Deoxyuridine creates a significant problem for thymidine purification. Therefore, one way to reduce deoxyuridine production is to efficiently convert dUMP to dTMP by increasing the level or effectiveness of thymidylate synthase such that the internal concentration of dUMP always remains very low.

The thymidylate synthase gene (td) may be heterologous with respect to the host cell and it is preferred that td is derived from (in the sense defined supra) T bacteriophage, e.g. T "even" phage and in particular T4 phage td. Although td may be located in its own transcription unit, it is preferred that td is located in the same transcription unit e.g. operon as nrd genes. Moreover, it is preferred that td is located in the same operon downstream (in terms of reading frame) from the nrd genes.

McCandliss and Anderson, supra, amplified the *E. coli* thymidylate synthase gene in plasmids pCG138 and pCG148 (see Table 5, of the '972 patent) and it was found to be partially effective in reducing deoxyuridine. The T4 thymidylate synthase is much more effective which is surprising in light of the fact that the *E. coli* enzyme is not thought to be controlled by any type of allosteric regulation (Neuhard and Kelln, supra). The *E. coli* enzyme $K_m$ for dUMP, 4 μM (Wahba, A. J. and M. Friedkin, *J. Biol Chem.* 237: 3794-3801), and the T4 enzyme $K_m$ for dUMP, 2.73 μM (Maley, F., L. LaPat-Polasko, V. Frasca and G. F. Maley, Functional domains in T4 Thymidylate Synthase as probed by site-directed mutagenesis, Chapter 29 [In] Karam, J. D. [ed] "Molecular Biology of Bacteriophage T4", American society for Microbiology, Washington, D.C., 1994, pp 322-325), are similar and cannot explain the large difference in effectiveness. Whilst not being bound by theory, the inventors believe that the *E. coli* thyA has an internal transcription termination sequence derived from an upstream gene that could be effecting the expression level in plasmid clones (Bell-Penderson, D, J. L. Galloway Salvo, and M. Belfort, *J. Bacteriol.* 173: 1193-1200, 1991).

In other preferred embodiments, host cells of the present invention, particularly for use in the commercial production of pyrimidine deoxyribonucleosides e.g. thymidine comprise a transcription unit (e.g. operon) which unit comprises DNA sequences e.g. udk gene encoding for uridine kinase and preferably DNA sequences e.g. dcd gene encoding for dCTP deaminase. See e.g. Wang, L. and B. Weiss, *J. Bacteriol.* 174:5647-5653 (1992); and Neuhard, J. and L. Tarpø, *J. Bacteriol.* 175: 5742-5743.

The construct of this aspect of the invention may additionally comprise a transcription unit encoding for ribonucleotide reductase (nrdA and nrdB) and the thioredoxin (nrdC), or precursor forms thereof which are preferably heterologous with respect to host cell DNA and preferably derived from *E.coli* bacteriophage, particularly T "even" phages e.g. T2,T4 or T6.

Uridine kinase produces UMP and CMP from uridine and cytidine using GTP (or dGTP) as the phosphate donor. The reaction is inhibited by UTP and CTP (J. Neuhard and R. D. Kelln, Biosynthesis and Conversions of Pyrimidines, Chapter 35 [in] F. C. Neidhart et al. [eds], "*Escherichia Coli* and *Salmonella* Cellular and Molecular Biology", Second Edition, ASM press, Washington D.C.). The present inventors have found that the use of uridine kinase particularly together with dCTP deaminase leads to a marked improvement in the production of thymidine by host cells incorporating these changes together with the teachings of '972 outlined supra. This observation is quite unexpected since uridine kinase, on the basis of current information, has no direct role in pyrimidine de novo biosynthesis, moreover that its use would be beneficial in commercial processes for the production of pyrimidine deoxyribonucleosides. It is preferred that udk and dcd genes are arranged in tandem in the same operon. Further envisaged are genes that encode precursor forms of the udk and dcd gene which are processed to produce a mature form. Such processing may proceed via various intermediate forms. The udk and dcd genes may be introduced into the construct (e.g. vector) from any suitable source by methods well known to those skilled in the art for example P1 transduction, electroporation or transformation.

The enzyme uracil DNA glycosylase, encoded by the ung gene, is responsible for degrading DNA that has uracil incorporated in place of thymine. Where host cells of the present invention are used in the commercial production of e.g. thymidine, the internal cellular concentration of dTTP may be lowered as a result of the utilization of dTMP (a precursor of dTTP) in the production of thymidine. Accordingly, the present inventors have recognized that there is potentially a greater propensity for uracil incorporation into the host DNA which may be lethal to a wild type host due to the uracil DNA glycosylase activity causing too many single stranded breaks in the host cell DNA. Thus, host cells useful in the present invention may further display repressed (compared to the unmodified cell) or no uracil DNA glycosylase activity. This repression or absence may be achieved through various ways apparent to those skilled in the art. For example, antagonism (either total or partial) of the ung gene expression products is one such approach by introducing an antagonist of the functional enzyme (or precursor thereof) into the host cell. Other approaches include manipulating ung gene expression by e.g. modifying regulatory elements of ung gene expression or introducing mutations into the ung gene itself such that ung gene product expression displays little or no uracil DNA glycosylase protein and/or activity. Another approach is to delete the ung gene (or functionally critical parts thereof) from host cell DNA. The absence or low level of uracil DNA glycosylase activity may be a feature of the host cell without the need for further manipulation.

In preferred embodiments of the present invention, each of the advances taught herein are incorporated into a host cell. The nrd, td, udk and dcd genes may be located on separate constructs but it is preferred that they are all located on the same construct e.g. vector. Thus in a particularly preferred embodiment of the present invention, a modified host cell is provided in which the cell comprises a DNA construct (e.g. vector) comprising a transcription DNA unit (e.g. operon) which unit comprises DNA sequences encoding for (preferably a T even phage, e.g. T4) a modified ribonucleotide reductase and thioredoxin in which said reductase preferably displays less sensitivity to allosteric inhibition than wild type host cell equivalent or counterpart wherein said construct further comprises:

(a) a transcription unit (e.g. operon) encoding for (preferably heterologous with respect to host cell equivalent or counterpart) thymidylate synthase and;

(b) a transcription unit (e.g. operon), encoding for uridine kinase and preferably dCTP deaminase;

and in which the host cell displays repressed or absent uracil DNA glycosylase activity.

Host cells modified according to the present invention are particularly useful in the commercial production of pyrimidine deoxynucleosides. In a particularly advantageous use of the present invention, *E. coli* host cells comprising (harboring) a plasmid modified according to the present invention (particularly in conjunction with the teachings of the '972 patent) may be used in the commercial production of thymidine. Thus, host cells modified according to the present invention may further comprise dTMPase derived from e.g. PBS1 and the mutations taught in the '972 patent, e.g. deoA, tdk-1 and udp-1.

Generally, a fermentation method is employed which involves submerging the cells in a culture medium contained within a suitable vessel. Following culturing under appropriate conditions, produced thymidine is harvested and purified (enriched), if necessary, to pharmaceutical grade according to standard protocols. The purified thymidine may then be used in the production of medicaments, e.g. pharmaceutical compositions such as AZT.

BRIEF DESCRIPTION OF THE DRAWINGS

The present invention is illustrated by way of example only and with reference to the following figures in which.

EXAMPLE 1

Cloning of T4 nrdCAB Genes and Demonstration of Activity

The bacteriophage T4 nrdAB genes were cloned by performing the polymerase chain reaction (PCR) with isolated phage T4 DNA. The primers for PCR nrdA gene were: 5'-TAT TCT AGA CGA TTT TCA AGT TGA GGA CTT ATG C-3'SEQ ID NO: 1); and 5'-TAT ATC GAT AAT TCA TTA CAA TTT ACA CGC TGC AC-3' (SEQ ID NO: 2).

The restriction site XbaI was the introduced at the beginning of the nrdA in the amplified DNA, and ClaI was introduced at the 3' end of nrdA. The primers for PCR amplification of nrdB gene were:

```
                                          (SEQ. ID NO:3)
5'-TAT ATC GAT AAA TGT AAA TTT AAG GAT TCT AAA

TG-3'
and
                                          (SEQ. ID NO:4)
5'-TAT GTC GAC TCC TTA AAA GTA TTT TTT AAA ACT

C-3'.
```

Figure 1:
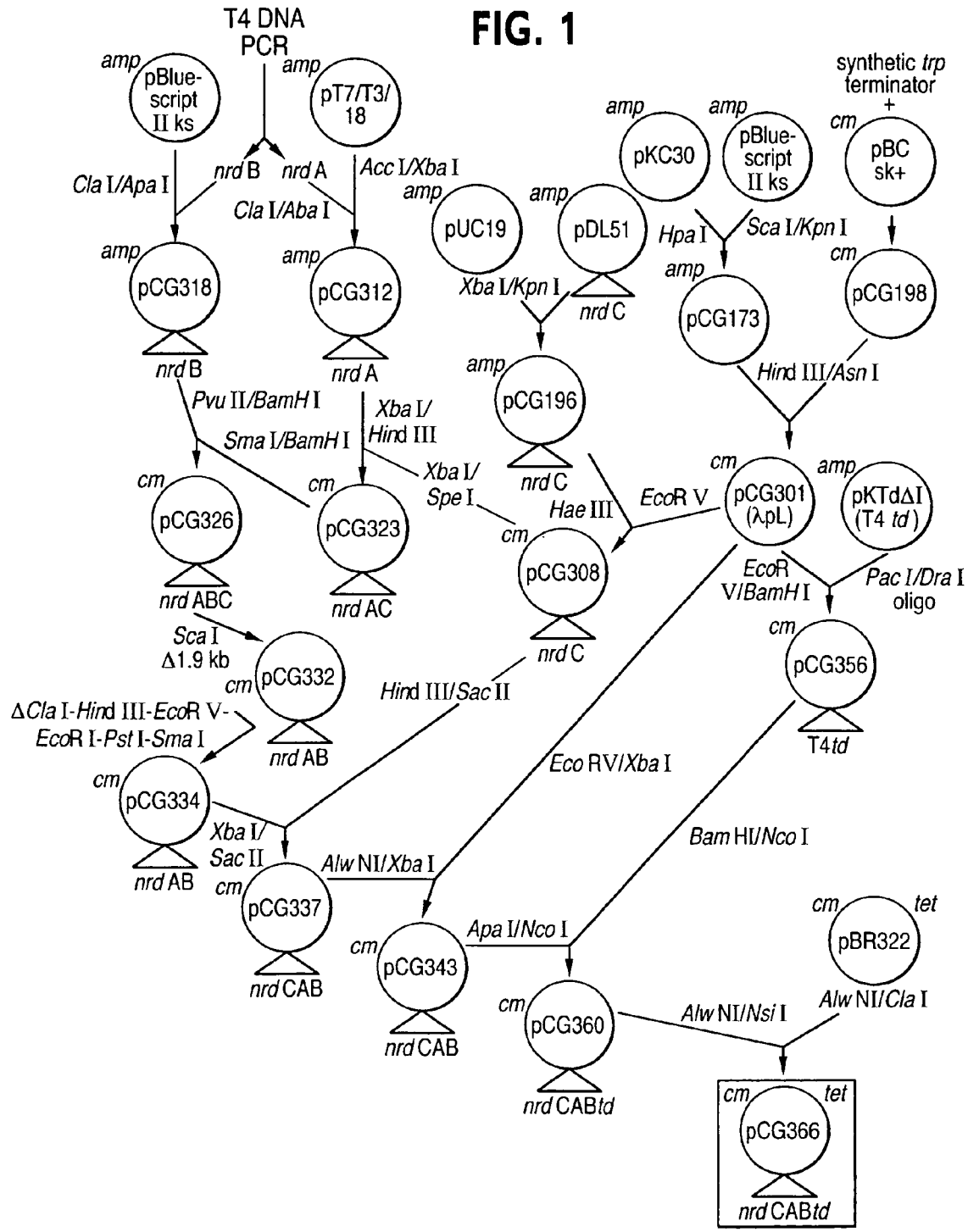
FIG. 1 illustrates, schematically, a route for the construction of pCG366. It should be noted that the plasmids are not drawn to scale.

The restriction site ClaI was thus introduced at the beginning of the nrdB, and ApaI was introduced at the end of nrdB in the amplified DNA. The PCR fragments were cloned into plasmid vectors as illustrated in FIG. 1 according to techniques known to those skilled in the art. The cloned nrdAB genes were confirmed by enzyme activity assay. The T4 nrdC gene was cloned into pKC30 producing plasmid pDL51 (LeMaster, D. M., *J. Virology* 59: 759-760, 1986 ) and was supplied by D. LeMaster (Dept of Biochem., Univ. Wisconsin, Madison, Wis.). The gene was sub-cloned into a plasmid with nrdAB genes as illustrated in the FIG. 1. The sources of starting materials and background information used in FIG. 1 are listed in Table 1.

A synthetic transcriptional terminator was used for the construction of pCG198 and pCG301(see FIG. 1 and Table 1). Specifically, plasmid pBC sk.sup.+obtained from Stratagene (La Jolla, Calif.) was digested with restriction enzyme ApaI and Asp718I. Synthetic DNA containing the ECOTGP transcription termination sequence (d'Aubenton Carafa et al., *J. Mol. Biol.* 216: 839-843, 1990) was then ligated replacing the original sequence between ApaI and Asp718I endonuclease sites. This fragment recreated the ApaI recognition sequence, but destroyed the Asp 718 I recognition sequence in the new plasmid. The inserted DNA had the following composition 5'-CGAGC CCGCCTAATG AGCGGGCTTT TTT TT-3'3'-CCGGGCTCG GGCGGATTAC TCGCCCGAAA AAAAACATG-5' (shown as respective strands In SEQ ID NOs:5 and 6) produced from two oligonucleotides.

TABLE 1

Genealogy of Plasmid pCG366 and pCG532 and Materials Source

| Plasmid | Gene(s) | Promoter | Vector origin | Marker | Derivation |
|---|---|---|---|---|---|
| PACYC177 | amp kan | | p15A | amp kan | Chang and Cohen (1978) J. Bacteriol. 134: 1141-1156. ATCC 37031 |
| pBC sk+ | Cam | Plac | ColE1 | Cam | Stratagene, 11011 North Torrey Pines Road, La Jolla, CA 92037. |
| pBluescript II ks | Amp | Plac | colE1 | Amp | Stratagene, 11011 North Torrey Pines Road, La Jolla, CA 92037. ATCC 87047 |
| pBR322 | amp tet | | colE1 | amp tet | Bolivar et al. (1977) Gene 2: 95-113. |
| pDL51 | T4 nrdC | | colE1 | Amp | LeMaster, J. Virol. 59: 759-760, 1986 |
| pKC30 | Amp | $\lambda P_L$ | colE1 | Amp | Shimatake, and Rosenberg. (1981) Nature 292: 128. ATCC 37286 |
| PKTdΔI | T4 td | | colE1 | Amp | West et al. (1986) J.B.C. 261: 13446-13450. |
| pT7/T3/18 | Amp | phage T7/T3 | colE1 | Amp | Life Technologies, INC., 9800 Medical Center Dr., Rockville, MD 20897. |
| pTZ18U | Amp | | colE1 | Amp | Bio-Rad, 2000 Alfred Nobel Dr., Hercules, CA 94547. |
| pUC18 | Amp | Plac | colE1 | Amp | Yanisch-Perron et al. (1985) Gene 33: 103-119. ATCC 37253 |
| pUC19 | Amp | Plac | colE1 | Amp | Yanisch-Perron et al. (1985) Gene 33: 103-119. ATCC 37254 |
| pCG173 | $\lambda P_L$ vector | $\lambda P_L$ | colE1 | Amp | $\lambda P_L$ in pBluescript II ks |
| pCG196 | T4 nrdC | | colE1 | Amp | T4 nrdC in pUC19 |
| pCG198 | Cam | Plac | colE1 | Cam | Synthetic transcription terminator in pBC sk+ |
| pCG301 | $\lambda P_L$ vector | $\lambda P_L$ | colE1 | Cam | $\lambda P_L$ in pCG198 |
| pCG308 | T4 nrdC | $\lambda P_L$ | colE1 | Cam | T4 nrdC in pCG301, LeMaster, J. Virol. 59: 759-760, 1986 |
| pCG312 | T4 nrdA | PT7 | colE1 | Amp | T4 nrdA in pT7/T3/18 |
| pCG318 | NrdB | PT7 | colE1 | | T4 nrdB in pBluescript II ks |
| pCG323 | NrdAC | $\lambda P_L$ | colE1 | Cam | T4 nrdAC in pCG301 |
| pCG326 | NrdABC | $\lambda P_L$ | colE1 | Cam | T4 nrdABC in pCG301 |
| pCG332 | NrdAB | $\lambda P_L$ | colE1 | Cam | T4 nrdAB in pCG301 |
| pCG334 | NrdAB | $\lambda P_L$ | colE1 | Cam | T4 nrdAB in pCG301 |
| pCG337 | NrdCAB | $\lambda P_L$ | colE1 | Cam | T4 nrdCAB in pCG301 |

TABLE 1-continued

Genealogy of Plasmid pCG366 and pCG532 and Materials Source

| Plasmid | Gene(s) | Promoter | Vector origin | Marker | Derivation |
|---------|---------|----------|---------------|--------|------------|
| pCG343 | NrdCAB | $\lambda P_L$ | colE1 | Cam | T4 nrdCAB in pCG301 |
| pCG356 | Td | $\lambda P_L$ | colE1 | Cam | T4 td in pCG301 |
| pCG358 | dcd, udk | | colE1 (pUC18) | Amp | E. coli dcd, udk in pUC18 |
| pCG360 | NrdCAB, td | $\lambda P_L$ | colE1 | Cam | T4 nrdCAB td in pCG301 |
| pCG366 | NrdCAB, td | $\lambda P_L$ | colE1 (pBR322) | Cam Tet | T4 nrdCAB, td in pBR322, $Amp^S$ |
| pCG374 | dcd, udk | | p15A | amp | E. coli dcd, udk in pACYC177 |
| pCG376 | $\lambda P_L$ vector | $\lambda P_L$ | p15A | amp | pACYC177 with $\lambda P_L$ & MCS of pCG301 |
| pCG464 | T4 nrdA XbaI/HindIII fragment | — | (pTZ18U) colE1 | Amp | XbaI/HindIII fragment with nrdA sequence cloned into XbaI/HindIII sites of pTZ18U (BioRad Laboratories) |
| pCG492 | T4 nrdA XbaI/HindIII Fragment | — | (pTZ18U) colE1 | Amp | PCG464 with mutation in T4 nrdA sequence causing $^{79}$ala → ile alteration |
| pCG494 | NrdCAB td | $\lambda P_L$ | colE1 (pBR322) | Cam Tet | KpnI/AflII fragment from pCG494 inserted into pCG366 adding $^{79}$ala → ile mutation to nrdA |
| pCG532 | NrdCAB, td, udk, Dcd | $\lambda P_L$ | colE1 (pBR322) | Cam | udk, dcd cloned into pCG494 | between Apa I and Asp718 I endonuclease sites. This fragment recreated the Apa I recognition sequence, but destroyed the Asp 718 I recognition sequence in the new plasmid. The inserted DNA had the following composition

```
5'   -CGAGC CCGCCTAATG AGCGGGCTTT TTT TT-3'

3'-CCGGGCTCG GGCGGATTAC TCGCCCGAAA AAAAACATG-5'
```

(shown as respective strands in seq. id 5 and 6) produced from two oligonucleotides.

Plasmid pCG198 was combined with pCG173 that contains the lambda $P_L$ promoter from plasmid pKC30 cloned into pBluescript II ks (Stratagene, La Jolla, Calif.) as shown in FIG. 1. Both pCB198 and pCG173 were digested with Hind III and Asn I then ligated to create new plasmid pCG301 containing the lambda $P_L$ promoter, multiple restriction enzyme cloning sites, and followed by the ECOTGP terminator sequence copied from the tryptophan operon leader peptide region.

T4 ribonucleotide reductase activity was measured by HPLC by a method that does not involve the use of radioisotopes and UDP substrate. The direct ribonucleotide reductase assay contained 1 mM NADPH, 1 mM DTT, 0.5 mM dATP, 0.6 mM UDP, 20 mM Tris (pH 8.0) and 5 mM $MgCl_2$. Under these conditions the E. coli ribonucleotide reductase is inhibited and is not detected. The enzyme reaction (100 μL) was stopped by the addition of 10 μL of 50% trichloroacetic acid (TCA). After 10 minutes on ice, the samples are centrifuged in a microcentrifuge. The supernatant was extracted 4 times with diethylether to remove the TCA. Five ml of Tris buffer (1.0 M pH 8.0) was added followed by 2 μL of 40 mg/mL rattle snake venom (Sigma), and the sample was incubated at 37° C. for 60 minutes. The samples were then heated for 3 minutes at 70° C. followed by centrifugation for 5 minutes to remove precipitate. The volumes are equalized, then analysed by HPLC with an UV detector and deoxyuridine as the standard. The column is a Spherisorb ODS-2, 5 micron, 250 mm×4.6 mm using a 12 mM ammonium phosphate (pH 5.0) mobile phase and a flow rate of approximately 1.0 mL/minute. Results are shown in Table 2 for cells containing plasmid pCG343 demonstrating functional expression of T4 ribonucleotide reductase.

TABLE 2

Ribonucleotide Reductase Activity

| Strain | Induction condition | Specific Acitivity nmol/10 min./mg protein |
|--------|---------------------|---------------------------------------------|
| CMG1093 | Uninduced | 0 |
| CMG1093 | Induced | 0 |
| CMG1093/pCG343 | Uninduced | 0 |
| CMG1093/pCG343 | Induced | 704.7 |

EXAMPLE 2

Derivation of Host Strain CMG2451 from Strain CMG1115

Strain CMG1115 is fully described in McCandliss & Anderson (U.S. Pat. No. 5,213,972). CMG1115 was the starting point for development described herein. Strain CMG1115 was improved for thymidine productivity by selection for growth on medium containing 30 mg/L of 5-fluorouridine that yielded strain CMG2401. Strain CMG2401 was then selected for growth on medium containing 30 mg/l of 3'-azido-3'-deoxythymidine which yielded strain CMG2404. CMG2404 requires L-proline for growth due to the inherited mutation Δ(lac-pro) from its original parent JM101. Hfr mating between CMG2404 and a Hfr stain CAG5053 (Singer, M. et al. Microbiological Review: 5:1-24,1989) was performed according to techniques known to those skilled in the art and yielded strain CMG2434 which is $Lac^+$, $Pro^+$. The udp (uridine phosphorylase) mutation in CMG2434 still had partial uridine phosphorylase activity that was evident based on thymine accumulation after induction of thymidine production. The udp mutation was reintroduced from CGSC5128 (E. coli Genetic Stock Center, Yale University) by phage P1 transduction according to techniques known to those skilled in the art. The metE3079::Tn10 from strain CAG18491 was first transduced into CMG2434 to serve as a positive selection marker for transduction of udp. Then the udp-1 was transduced into the metE3079::Tn10 derivative of CMG2434 by selecting for growth without L-methionine in the defined medium. The udp-1 derivative was named strain CMG2451. The genealogy of CMG2451 is summarized in Table 3.

TABLE 3

Genealogy of E. coli Host Strain CMG2451

| Strain | Genotype | Derivation[a] |
|---|---|---|
| CMG1115 | CMG1106 (Tn5::dTMPase kan[R]) | Tn5::dTMPase insertion from pCG132. |
| CMG2401 | CMG1115 FUdR[R] | 5-fluoro-2'deoxyuridine resistance. |
| CMG2404 | CMG2401 AZT[R] | 3'-Azido-3'deoxythymidine resistance. |
| CMG2434 | CMG2404 Lac[+] Pro[+] | Repair Δ(lac-proAB) by conjugation with CAG5053[b]. |
| CMG2448 | CMG2434 metE3079::Tn10 | metE3079::Tn10 from CAG18491[b]. |
| CMG2451 | CMG2448 udp-1 metE[+] tet[a] | udp-1 from CGSC5128[c] and replaced metE3079::Tn10. |

[a]Mutations were at times introduced into E. coli strains by phage P1 transduction. If the mutation has a selective marker, direct P1 transduction was used. If the mutation has no selective marker, P1 cotransduction with the nearby Tn10 insertion was used.
[b]Singer, M., et al. Microbiological Review: 53: 1-24, 1989.
[c]All CGSC strains can be obtained for E coli Genetic Stock Center, Yale University, P.O. Box 208104, New Haven, CT 06520-8104.

EXAMPLE 3

Cloning and Expression of T4 td Gene into Thymidine Production Plasmid

The T4 td gene was cloned into pKTd.DELTA.I by West et al. (J. Biol. Chem 261:13446-13450, 1986) without the 1017-base pair intron. The td gene was sub-cloned into pCG301using two oligonucleotides as linkers with the following sequences:

```
                                             (SEQ. ID NO:7)
5'-GAT CCG GAG GAT AAA TGA AAC AAT ACC AAG ATT

TAA T-3'
and;
                                             (SEQ. ID NO:8)
5'-TAA ATC TTG GTA TTG TTT CAT TTA TCC TCC G-3'.
```

The result plasmid was pCG356. The td gene from pCG356 was then sub-cloned into pCG343 to create pCG360 (FIG. 1). The tetracycline resistance gene and plasmid replication origin from pBR322 (Bolivar, F. et al., Gene 2: 95-113, 1977) was sub-cloned into pCG360 and formed pCG366. The thymidylate synthase activity was measured by spectrophotometric method of Wahba and Friedkin (J. Biol. Chem. 236: PC11-PC12, 1961 ). The results are shown in Table 4.

TABLE 4

Thymidylate Synthase Activity

| Strain | Specific Activity ΔOD340/mg protein/min |
|---|---|
| CMG1093 | −0.72 |
| CMG1093/pKTdDI | 3.24 |
| CMG1093/pCG356 | 3.45 |
| CMG1093/pCG360 | 1.43 |

EXAMPLE 4

Shake Flask Data Showing the Value of T4 td Gene on Thymidine Production and Deoxyuridine Reduction The shake flask fermentation was used to evaluate the thymidine productivity of different E. coli recombinants. The shake flask fermentation broth and methods used here, and in other examples, is described in Example 6 below. In this case 20 mL volume per flask was inoculated with 2 ml of seed culture and incubated in a 30° C. shaker. At about 10 OD 600 nm, the flasks were transferred into a 37° C. shaker for 30 minutes to mildly induce the $\lambda P_L$ promoter. Then the flasks were transferred into a 35° C. shaker to continue the fermentation. Glucose was fed during fermentation as needed, and pH was adjusted to about 7 with ammonia according to the color of phenol red. The thymidine concentration was measured by HPLC using a Spherisorb ODS-2, 5 micron, 250-mm×4.6 mm column, and a 25 mM ammonium phosphate (pH 3.3) mobile phase with a flow rate of approximately 1.5 ml/minute.

The strain CMG2451/pCG366 (T4 nrdCAB, td) was compared with CMG2451/pCG343 (T4 nrdCAB) in shake flask fermentation. Table 5 shows that deoxyuridine concentration was reduced, and converted to thymidine in strain CMG2451/pCG366 due to the T4 td gene.

TABLE 5

Thymidine Production-Effect of Thymidylate Synthase at 66 hours.

| Stain | Thymidine (mg/l) | Deoxyuridine (mg/l) | % Deoxyuridine |
|---|---|---|---|
| CMG2451/pCG343 | 1198 | 1728 | 144.2 |
| CMG2451/pCG366 | 3327 | 206 | 6.2 |

EXAMPLE 5

Construction of the [79]Ala to Ile T4 Ribonucleotide Reductase Mutant

The mutation was introduced by using site-directed mutagenesis based on a method described by Kunkel (Kunkel, T. A., Proc. Natl. Acad. Sci. USA, 82:488-492, 1985). All materials for mutant construction including pTZ18U phagemid DNA, M13KO7 helper phage, bacterial strains E. coli 0J236 and MV1190, T7 DNA polymerase and T4 DNA ligase were provided in the Muta-Gene in vitro mutagenesis kit from Bio-Rad Laboratories (Hercules, Calif.). At first, the XbaI/HindIII DNA fragment containing the nrdA gene of T4 bacteriophage was isolated from plasmid pCG312 (ChemGen Corp., Table 1 above). The XbaI/HindIII DNA fragment was cloned into the XbaI/HindIII sites of the pTZ18U phagemid vector using standard protocols (Sambrook, J., Fritsch, E. F. and Maniatis, T., Molecular Cloning, Cold Spring Harbor Laboratory, New York, 1989). The insert-carrying phagemid pCG464 was introduced into E. coli CJ236. This strain is deficient for dUTPase (dut) and uracil-N-glycosylase (ung) which results in an occasional substitution of uracil for thymine in newly synthesized DNA. Single stranded DNA of pCG464 containing uracil was isolated from CJ236 according to Bio-Rad Laboratories Instructional Manual. This DNA (0.2 pMole) was annealed with 6 pMole of phosphorylated primer 5'-AGC AAA CAT TAA ACA GCG TGC AATTAC ATA TTG ATA ATC AGG TTC-3'(SEQ ID NO: 9) containing the sequence of the desired mutation (underlined) coding for Ile instead of original .sup.79 Ala.

Complementary strand DNA was synthesized by using T7 DNA polymerase as described in the Bio-Rad protocol. The reaction products were transformed into E. coli MV1190 containing a wild type uracil-N-glycosylase, which degrades the uracil-containing parental strand, thus enriching for the mutant strand. Direct DNA sequencing using the Silver Sequence DNA Sequencing System from Promega Corp. (Madison, Wis.) identified plasmids containing the desired mutation. It appeared that all four analysed transformants contained plasmids with the mutation. One of them was designated pCG492 and used for further experiments. To check if the mutation affects thymidine synthesis it was introduced into production plasmid pCG366 (ChemGen Corp., Table 1 and FIG. 1). For this, the KpnI/AflII DNA fragment of pCG366 containing 5'-part of the nrdA gene was replaced with KpnI/AflII fragment from pCG492 that contains the mutation. The new plasmid pCG494 was introduced into production strain CMG2451 (ChemGen Corp., Example 2 and Table 4 above). The effect of T4 nrdA mutation was evaluated by comparison of thymidine production by CMG2451 (pCG494) and CMG2451 (pCG366) as shown in Example 6 below.

EXAMPLE 6

Shake Flask Fermentation for Thymidine Production Using CMG2451 (DCG366) and CMG2451 (pCG494)

The 250-mL baffle flasks containing 25 mL of production medium were inoculated with 2 mL of a freshly grown seed culture in LB broth with appropriate antibiotic added. The cultures were grown in a 30° C. shaker at 250 rpm. When the $OD_{600}$ reached about 5, the flasks were transferred into a 37° C. shaker for 30 min. Then the flasks were transferred into a 35° C. shaker to continue the fermentation. The production medium has the following composition (g/L): Ardamine YEP-S (Red Star Yeast & Products, Milwaukee, Wis.)—10; $CaCO_3$—10; $MgSO_4$—0.4; phenol red—0.24; PP90BT (DMV International, Fraser, N.Y.)—4.5; sorbitol—20; chloramphenicol—0.03; trace elements (1000×)—1 mL/L. The trace elements (1000×) formulation is the following (g/L): boric acid—0.05; calcium chloride—20; cobalt sulfate—0.05; copper sulfate—0.01; ferrous sulfate—20; ferric chloride—20; manganese sulfate—0.5; sodium molybdenate—0.1; and zinc sulfate—0.1. At the time of induction 10 grams per liter of Ardamine YEP-S was added. Glucose was fed during the fermentation on an average of every two hours (2.5 g/L). The pH in the flasks was maintained at approximately 7.0 through the addition of 4N $NH_4OH$ as judged by the color of the phenol red indicator dye. The $OD_{600}$ was read after sample dilution 1:10 into 10 mM $H_2SO_4$ to dissolve salts in the medium. Thymidine concentration was measured by reverse phase C-18 HPLC with an Alltech Spherisorb ODS-2 column and Shimadzu spectrophotometric detector at 260 nm. The mobile phase was a 25 mM $NH_4H_2PO_4$ (pH 3.3) in water at the constant rate of 1.5 mL/min.

The results of thymidine production by CMG2451 (pCG366) and CMG2451 (pCG494) after 2, 17 and 25 hours after induction are presented in Table 6. There were two repeats of the flasks in this experiment and variability between duplicate flasks did not exceed 15%. The results show that the T4 nrdA mutant performed better than the wild type nrdA strain. This was confirmed in several independent shake flask experiments with the same bacterial strains.

TABLE 6

| Thymidine production by CMG2451 (pCG366) and CMG2451 (pCG494) | | | |
|---|---|---|---|
| Strain | 2 hours | 17 hours | 25 hours |
| | Specific activity (mg/L/OD) | | |
| CMG2451 (pCG366) | 6.1 | 32.5 | 43.1 |
| CMG2452 (pCG494) | 8.5 | 36.1 | 51.4 |

EXAMPLE 7

Figure 2:
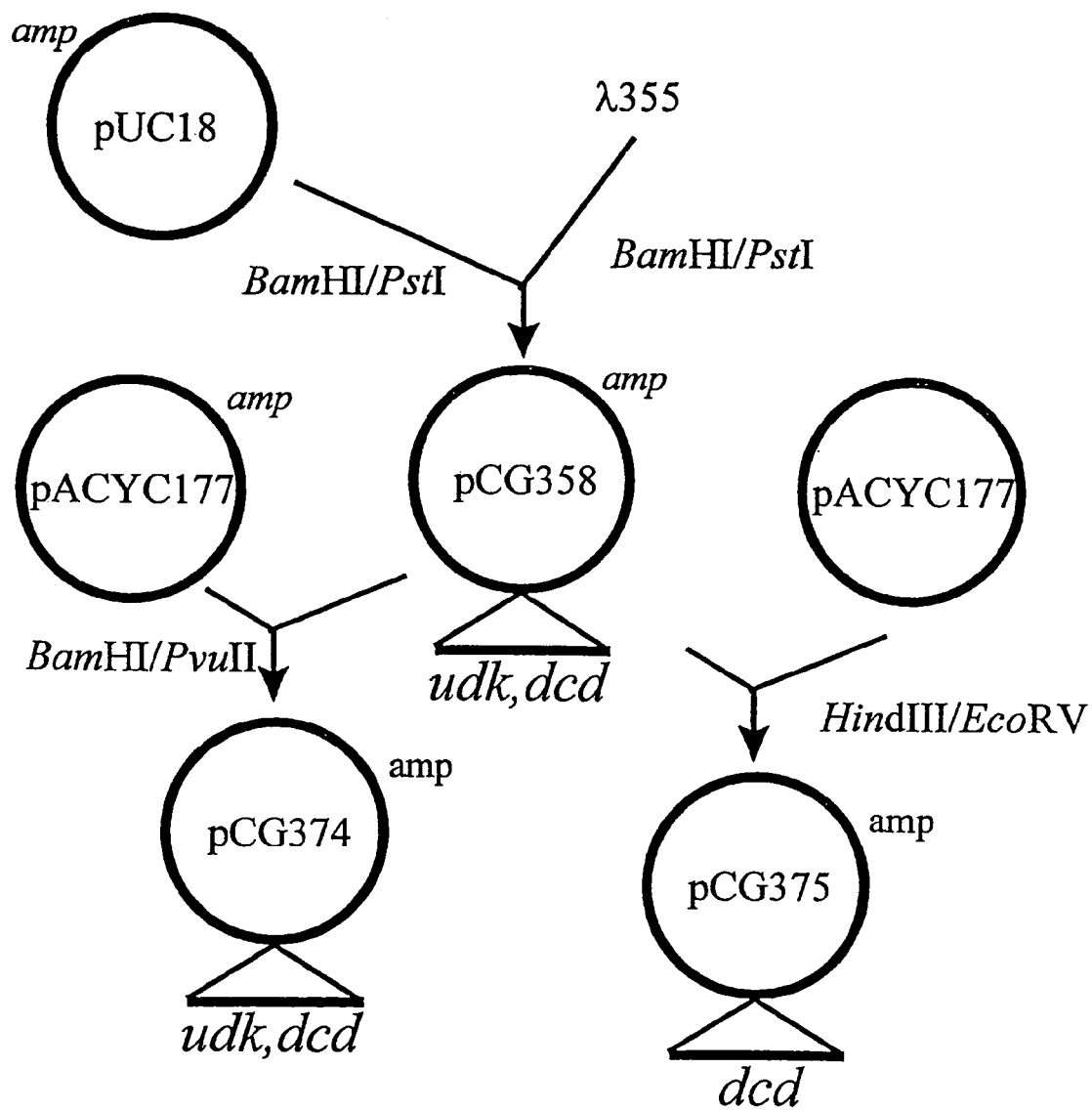
FIG. 2 illustrates, schematically, a route for the construction of pCG374 and pCG375.

Shake Flask Fermentation to Demonstrate the Effect of the E. coli udk Gene on Thymidine Production The dcd gene or dod udk operon were cloned into the pACYC177 vector. This vector with the p15a origin of replication is different from colE1 based plasmids such as pCG366 and thus is compatible and can be maintained in the same host with colE1 based plasmids. The details of the plasmid constructions resulting in pCG374 (udk dcd) or pCG375 (dcd) are shown in FIG. 2. The genes on these plasmids are expressed from the native E. coli promoter of the udk dcd operon.

Using selection for ampicillin resistance, plasmids pCG374 and pCG375 were introduced into CMG2451 (pCG366) to test the effect on thymidine production in the shake flask fermentation method described in Example 6. The results at several time points are shown in Table 7. Although the specific activity (thymidine per OD of cells) is similar both with and without the udk gene, the cells with the udk gene on the second plasmid pCG374 grew to a higher cell density and produced significantly more thymidine (5.8 g/L compared to 3.0 g/L for the strain with the dcd only second plasmid). This result was not anticipated, as it is not clear why uridine phosphorylase could have this effect.

Figure 3:
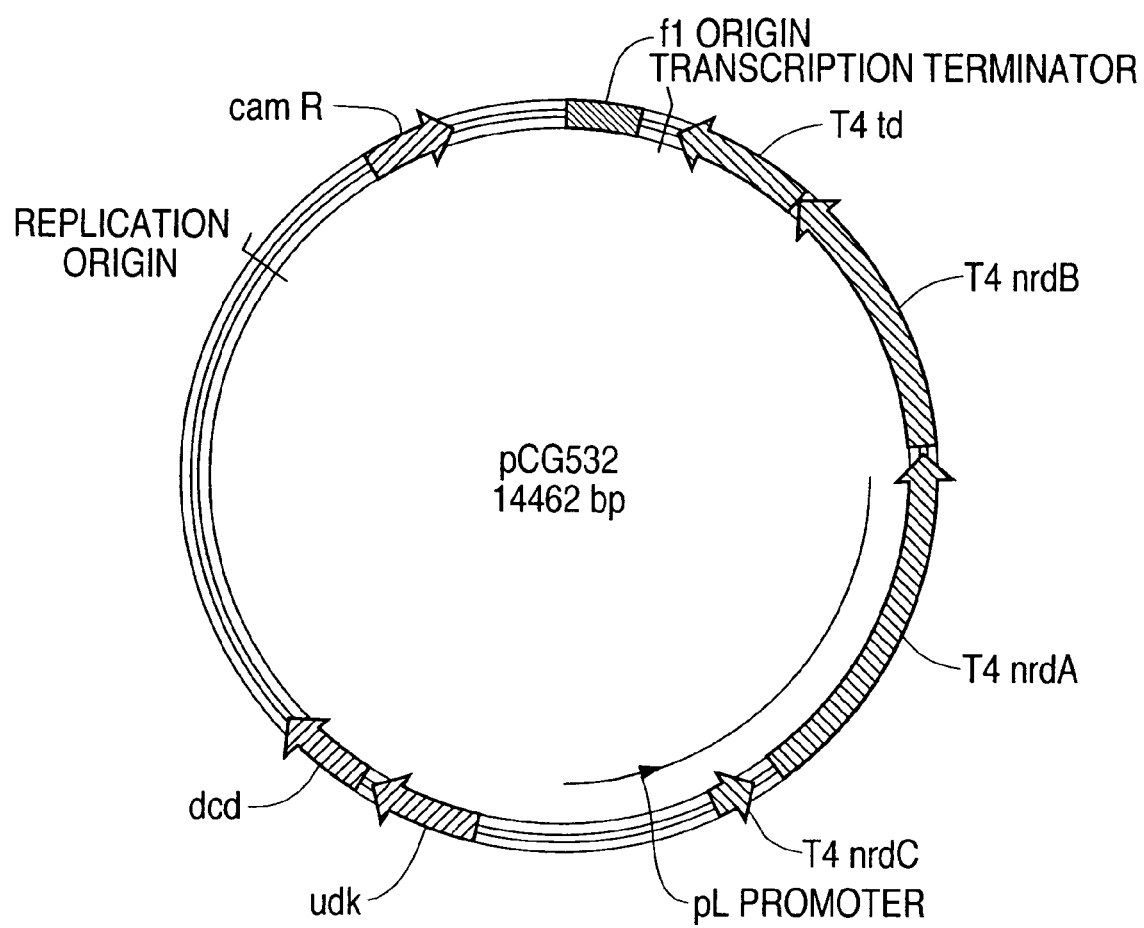
FIG. 3 illustrates a map for plasmid pCG532.

Based on this data and other information, the udk gene was chosen for introduction along with the E. coli dcd gene in the construction of plasmid pCG532 (see Example 8 and FIG. 3).

TABLE 7

Comparison of the effect of second plasmids with dcd or dcd udk on thymidine production in the CMG2451 (pCG366) background.

|  | O.D.600 | | Thymidine (mg/l) | | Specific Thymidine (mg/l/OD) | |
| --- | --- | --- | --- | --- | --- | --- |
| Base Strain And Plasmid | | | | | | |
|  | CMG241 (pCG366) | CMG2451 (pCG366) | CMG2451 (pCG366) | CMG2451 (pCG366) | CMG2451 (pCG366) | CMG2451 (pCG366) |
| Second pACYC 177 based plasmid | | | | | | |
| Time (hour) | PCG374 with dcd udk | pCG375 with dcd | pCG374 with dcd udk | pCG375 with dcd | pCG374 with dcd udk | PCG375 with dcd |
| 8 hr | 29.112 | 29.94 | 889 | 884 | 30.5 | 29.5 |
| 18 hr | 40.206 | 32.946 | 1721 | 1608 | 42.8 | 48.8 |
| 42 hr | 48.348 | 33.96 | 4020 | 2740 | 83.1 | 80.7 |
| 66 hr | 57.498 | 28.614 | 5804 | 3012 | 100.9 | 105.3 |

EXAMPLE 8

Cloning of the E. coli udk dcd Operon Into Production Plasmid pCG494

The udk and the dcd genes of *E. coli* encode pyrimidine ribonucleotide kinase and dCTP deaminase, respectively. Both genes were mapped to a 3.4 kb BamHI/PstI DNA fragment of lambda phage 355 of the Kohara genomic library (Kohara, Y., Akiyama, K. and Isono, K., *Cell* 50, 495-508, 1987). It appears that udk is located upstream of dcd and transcribed in the same direction as dcd (Neuhard, J. and Tarpo, L., *J. Bacteriol.* 175: 5742-5743, 1993). The genes were cloned into production plasmid by two steps.

At first, a 3.4 kb BamHI/PstI DNA fragment from lambda 355 was cloned into the multiple cloning site of plasmid pUC18 (Yamisch-Perron, C., Vieira, J. and Messing, J., *Gene* 33: 103-109,1985) (plasmid pCG358). Then, the fragment was excised from the polylinker region of pCG358 with BamHI and SphI and cloned in place of a 0.7 kb BglII/SphI fragment (containing a portion of the tetracycline resistance gene) of production plasmid pCG494. The final 14.7 kb plasmid pCG532 contains colE1 compatibility group origin of replication, the chloramphenicol resistance gene, the udk and the dcd genes and the T4 bacteriophage nrdCAB (encode thioredoxin and two subunits of ribonucleotide reductase, respectively) and the T4 td (encodes thymidylate synthase) genes under control of the $P_L$ promoter of bacteriophage lambda. The T4 nrdA gene of pCG532 was previously changed by site-directed mutagenesis ($^{79}$Ala to Ile).

A synthetic transcriptional terminator is located downstream of the td gene to prevent transcriptional readthrough into the replication region. The genetic map of plasmid pCG532 is illustrated in FIG. 3.

EXAMPLE 9

Shake Flask Fermentation of Thymidine by CMG2451 (pCG494) and CMG2451 (pCG532)

Plasmid pCG532 containing the udk and the dcd genes of *E. coli* was introduced into production strain CMG2451. New strain CMG2451 (pCG532) was tested together with parent strain CMG2451 (pCG494) in shake flask experiments to compare thymidine production. The results of two independent experiments are shown in Table 8. The first experiment was performed as described above and samples were taken at 17 hours after induction. In the second experiment cells were induced at higher OD (about 9) and samples were taken at 3 hours after induction for analysis. In both cases the strain containing the cloned udk and dcd genes performed better than the parent strain.

TABLE 8

Thymidine fermentation by thymidine by CMG2451 (pCG494) and CMG2451 (pCG532)

| Strain | O.D 600 | TdR (mg/L) | Specific Activity(mg/L/OD) |
| --- | --- | --- | --- |
| Experiment 1 | | | |
| CMG2451 (pCG494) | 16.5 | 599 | 36.3 |
| CMG2451 (pCG532) | 17.5 | 867 | 49.5 |
| Experiment 2 | | | |
| CMG2451 (pCG494) | 8.5 | 149 | 17.5 |
| CMG2451 (pCG532) | 8.4 | 192 | 22.8 |

EXAMPLE 10

Figure 4:
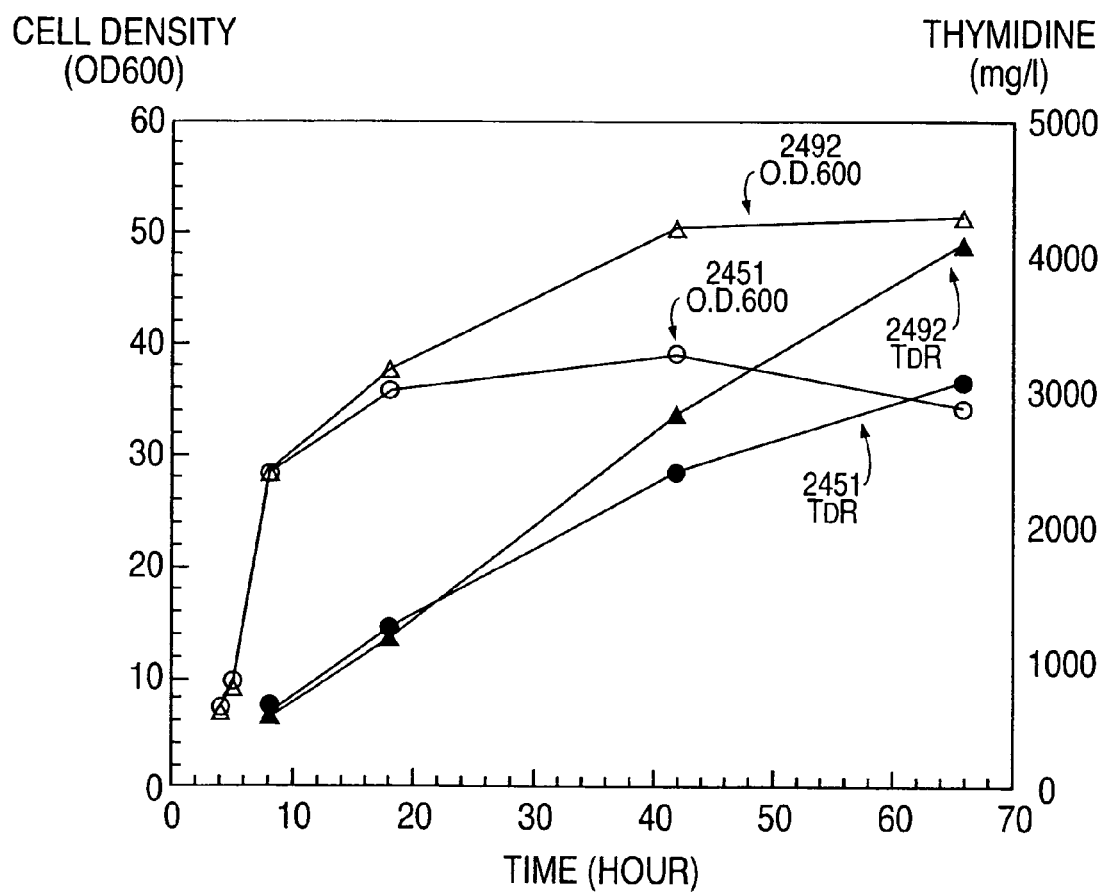
FIG. 4 illustrates growth and thymidine production by recombinant *E. coli* strain CMG2451 (Ung$^+$) and CMG2492 (Ung$^-$) hosting a plasmid pCG366 (nrdCAB td) according to example 10.

Addition of ung Mutation and its Effect on Thymidine Production in Shake Flask Fermentation An uracil DNA glycosylase negative strain was constructed by introducing an ung::Tn10 (Varshney, U., et al., *J. Biol. Chem.* 263:7776-7784,1988) mutation into host CMG2451 using P1 transduction as described above, and was named CMG2492. Plasmid pCG366 was introduced into CMG2492. A comparison experiment between Ung$^-$ and Ung$^+$ strain for thymidine synthesis in shake flasks is shown in FIG. 4 using the flask method described in Example 6. Cells were grown in 250 ml flasks at 30° C., and thymidine synthesis was induced by shifting temperature to 37° C. for 30 min, then, shifting to 35° C. The Ung⁻ host without uracil DNA glycosylase kept growing longer and made 30% more thymidine.

EXAMPLE 11

Thymidine Production in a 30 Liter Fermentor with Strain CMG2451 (pCG532)

The following conditions were used to produce thymidine in a 30-Liter fermentor (B. Braun Biotec Biostat C) with strain CMG2451/532. The seed culture (500 mL)was grown in a 4 Liter baffle shake flask in LB medium (5 g/L Difco yeast extract, 10 g/L Difco tryptone, 5 g/L NaCl) with 30 mg/L chloramphenicol and 25 mg/L kanamycin at 30° C. until 2.37 OD 600 nm was reached with a final pH of 6.69.

The initial batch in the fermentor (12 Liters) containing the composition listed in Table 9 was sterilized at 121° C. for 55 minutes. After cooling a separately autoclaved solution (500 mL) was added to adjust the batch to 20 g/L sorbitol and 3.0 g/L $MgSO_4.7 H_2O$. Also added before inoculation was a sterile filtered solution (200 mL) designed to to adjust the initial batch to 30 mg/L chloramphenicol, 25 mg/L kanamycin, 1 mg/L d-biotin, 10 mg/L thiamine and 10 mg/L nicotinic acid.

Three feed solutions were prepared: a) Cerelose 2001 (dextrose monohydrate) 562 g/L with 2 mg/L biotin, 20 mg/L thiamine, 20 mg/L nicotinic acid, and 30 mg/L chloramphenicol; b) sorbitol 717 g/L with with 4 mg/L biotin, 40 mg/L thiamine, 40 mg/L nicotinic acid, and 60 mg/L chloramphenicol; and c) crude nitrogen mixture containing 360 g/L Amberex 695 AG yeast extract (Red Star Yeast & Products, Milwaukee, Wis.), 6 g/L PP90M (DMV International, Fraser, N.Y.) with 1X trace elements and 0.1 mL/L Mazu DF10PMOD11 (BASF). The feed solutions were sterilized for 40 to 50 minutes under 18 PSI steam pressure.

TABLE 9

Initial batch composition In 30 L fermentor

| Component | Concentration (g/L or mL/L) |
|---|---|
| Sodium hexametaphosphate | 4 |
| $KH_2PO_4$ | 4 |
| $(NH_4)_2HPO_4$ | 4 |
| $CaCl_2$ | 0.4 |
| Citric acid | 0.5 |
| Amberex 695 (Red Star Yeast & Products, Milwaukee, WI) | 20 |
| PP90M (DMV International, Fraser, NY) | 15 |
| Tryptone (Difco, Detroit, MI) | 5 |
| 1000× Trace elements (see Example 7) | 1 mL/L |
| $CaCO_3$ | 5 |
| Glycine | 1.83 |
| Mazu DF10PMOD11 Defoamer (BASF Speciality Products, Gurnee, IL) | 0.2 mL/L |

The operating conditions were as follows: initial temperature 31° C.; RPM 600; air flow 3 LPM; pH 6.8; pressure 0 Bar. The dissolved oxygen was controlled at 25% saturation using air flow rate control loop. The RPM was increased to 750 RPM at 8 hours, 850 RPM at 9 hours and 950 RPM at the time of temperature shift from 31 to 35.5° C. at 9.2 hours when the culture reached 37.8 OD. Beginning at 9.7 hours back pressure was applied up to a maximum of 0.6 Bar to aid in oxygen transfer into the culture. The rate of temperature shift for induction of thymidine synthesis was 0.2° C. per minute.

After the cell mass reached 20 OD at 600 nm (read after dilution in 50 mM $H_2SO_4$ to dissolve salts), 85 mL batch feeds of the sorbitol feed solution (b) were made for each 5 OD increase in cell mass. At 16.7 hours sorbitol batch feeding was stopped and dextrose monohydrate (glucose) feed (a) was started under the control of the DO PID control loop of the B. Braun fermentor with a set point of 25%. Simply stated, when dissolved oxygen was below 25% sugar feed was off, and when DO was greater than 25% the sugar feed was set to on. The protocol self regulates the glucose concentration keeping the concentration low, but does not allow the culture to starve for glucose for a very prolonged length of time. Crude nitrogen feeds (500 mL) were made at 11 hours, 16.2 hours, 21.2 hours, 28.2 hours, 33.2 hours and 40.5 hours.

Figure 5:
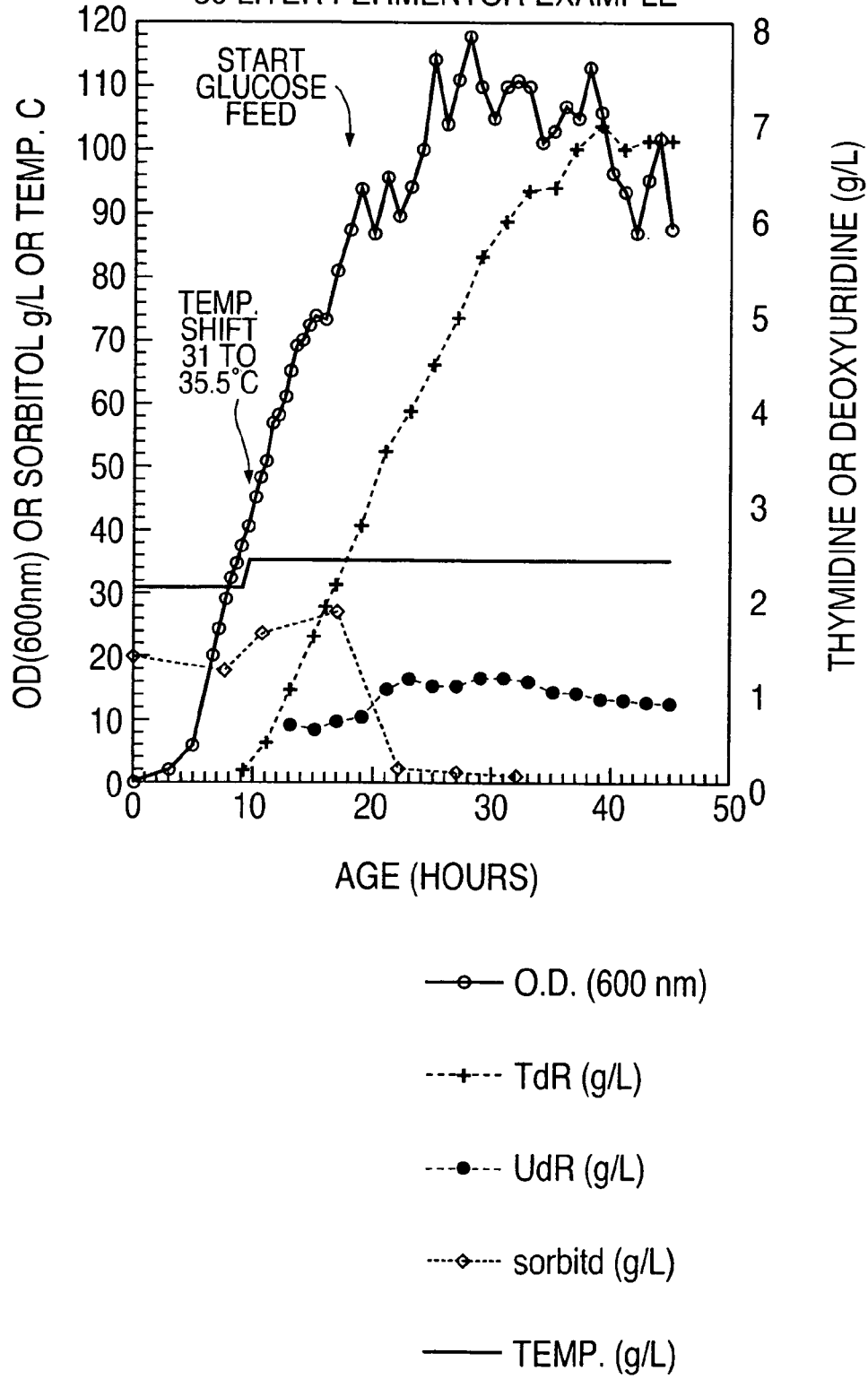
FIG. 5 illustrates thymidine production in a 30-liter fermentor by *E. coli* CMG2451 (pCG532).

The cell mass, thymidine and deoxyuridine accumulation during the fermentation are shown in FIG. 5.

EXAMPLE 12

Purification of Thymidine from Fermentation Broth

Dowex Optiptore-L-285 adsorbent (The Dow Chemical Company) was suspended in deionized water and packed into a 48 mM diameter glass column making a bed volume of about 500 mL. The column was washed with 500 mL of 5% NaOH, then washed with deionized water to until the effluent was pH 7.0

Figure 6:
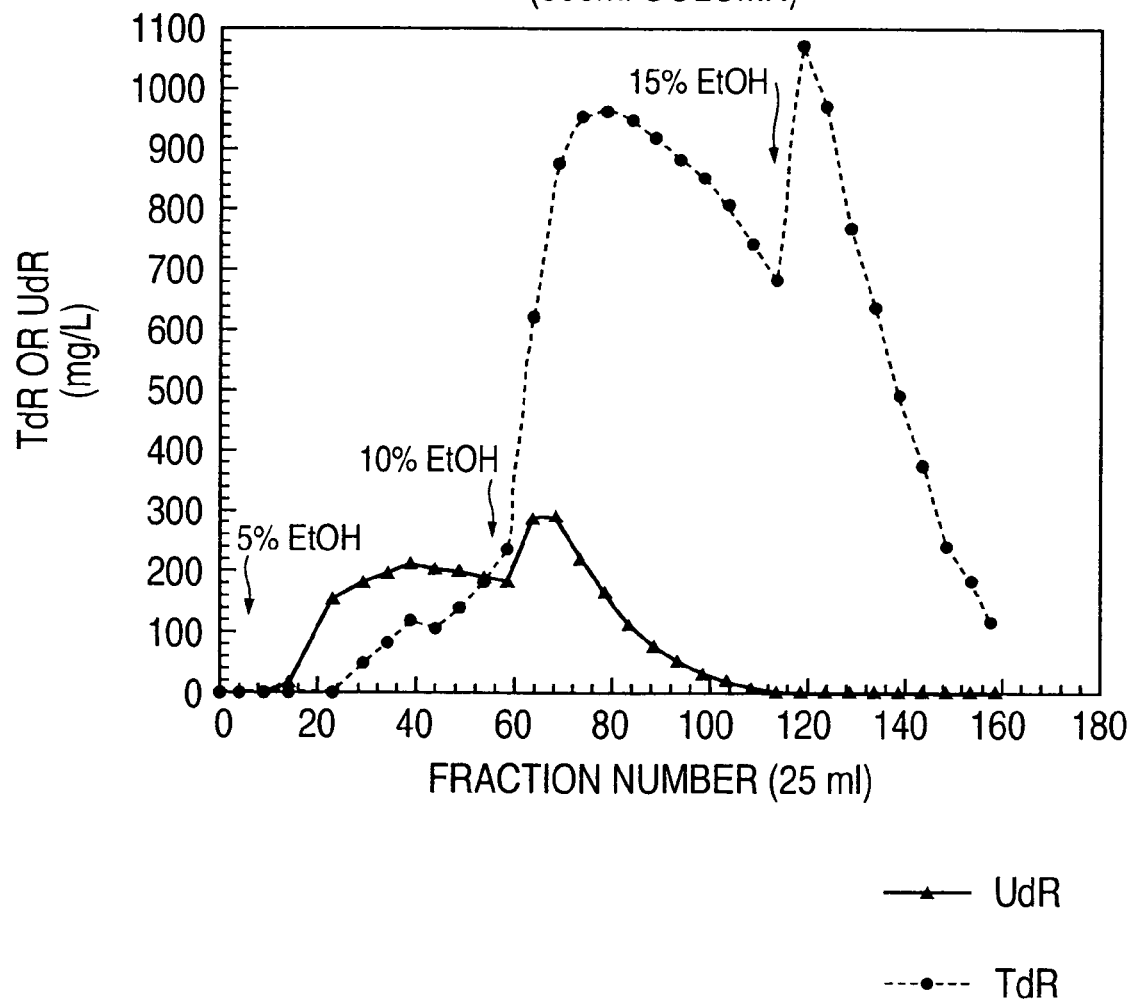
FIG. 6 illustrates TdR and UdR (mg/L) obtained according to the purification protocol of example 12.

500 mL Fermentation broth with thymidine (rdR) concentration of 4.890 g/L and deoxyuridine (UdR) concentration of 1.040 g/L was loaded onto the column. The column was washed with two bed volumes of deionized water. TdR and UdR were eluted by two bed volumes of 5% reagent alcohol (Ethanol 90.5%, Methanol 4.5%, Isopropyl alcohol 5%) followed by two bed volumes of 10% reagent alcohol and two bed volumes of 15% reagent alcohol. The TdR and UdR in the 25 mL fractions is shown in FIG. 6. The column was regenerated by washing with 5% NaOH, then with deionized water to pH7.0 and the procedure was repeated. The fractions 91-160 were pooled together from the two separate runs and dried using a rotary vacuum evaporator. Thymidine was redissolved in a minimal amount of hot water and crystallized at 4° C. Then the crystals were re-crystallized two times and dried in a 55° C. oven for 15 hours. A total of 979.8 mg of crystalline thymidine was obtained with a purity of greater than 99% that should be suitable for use as a pharmaceutical intermediate.

The side fractions containing both deoxyuridine and thymidine were pooled with mother liquors and reduced by a rotary vacuum evaporator to a final volume of 1200 mL with reduced alcohol. The total amount of TdR in this 1200 mL solution was 3571 mg. The total recovery (including the 3571 mg of TdR side fractions) was 93.1%.

SEQUENCE LISTING

<160> NUMBER OF SEQ ID NOS: 9

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 1
tattctagac gattttcaag ttgaggactt atgc                              34

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 2
tatatcgata attcattaca atttacacgc tgcac                             35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 3
tatatcgata aatgtaaatt taaggattct aaatg                             35

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 4
tatgtcgact ccttaaaagt attttttaaa actc                              34

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:  DNA insert
<220> FEATURE:
<223> OTHER INFORMATION: Part of a double stranded DNA insert. The
      non-overhanging part of SEQ ID NO: 6 is the
      complement

<400> SEQUENCE: 5
cgagcccgcc taatgagcgg gcttttttt                                    30

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: DNA insert
<220> FEATURE:
<223> OTHER INFORMATION: Part of a double stranded DNA insert. SEQ ID
      NO: 5 is the complement of the non-overhanging part of the
      sequence

```
<220> FEATURE:
<221> NAME/KEY: misc_feature
<222> LOCATION: (1)..(4)
<223> OTHER INFORMATION: Overhang
<220> FEATURE:
<221> NAME/KEY: misc_feature
<222> LOCATION: (35)..(38)
<223> OTHER INFORMATION: Overhang

<400> SEQUENCE: 6
gtacaaaaaa aagcccgctc attaggcggg ctcgggcc                              38

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
gatccggagg ataaatgaaa caataccaag atttaat                               37

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
taaatcttgg tattgtttca tttatcctcc g                                    31

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 9
agcaaacatt aaacagcgtg caattacata ttgataatca ggttc                     45
```

The invention claimed is:

1. A DNA construct comprising a transcriptional unit which comprises a wild type T4 ribonucleotide reductase gene, an *E. coli* uridine kinase gene and a dCTP deaminase gene.

2. A modified host cell comprising a DNA construct, which construct comprises a transcription DNA unit, which unit comprises a modified T4 nrdA gene comprising SEQ ID NO: 9 and a thioredoxin gene, and wherein said host cell further comprises one or more of the following features:
   (a) a transcription unit located on said DNA construct, comprising a thymidylate synthase gene heterologous to the thymidylate synthase gene of the host cell;
   (b) a transcription unit located on said DNA construct, comprising a uridine kinase gene; and
   (c) a transcription unit located on said DNA construct, comprising a dCTP deaminase gene.

3. The modified host cell of claim 2 wherein the host cell is an *E. coli* cell modified such that the host cell's endogenous ung gene is inactivated by an insertion in the ung gene.

4. A DNA construct comprising a transcriptional unit which comprises a modified T4 nrdA gene, an *E. coli* uridine kinase gene, and a dGTP deaminase gene, wherein the modified T4 nrdA gene comprises SEQ ID NO: 9.

* * * * *